United States Patent [19]

Bagga

[11] 4,284,574
[45] Aug. 18, 1981

[54] DIGLYCIDYL ETHERS OF DI-SECONDARY ALCOHOLS, THEIR PREPARATION, AND CURABLE COMPOSITIONS CONTAINING THEM

[75] Inventor: Madan M. Bagga, Cambridge, England

[73] Assignee: Ciba-Geigy Corporation, Ardsley, N.Y.

[21] Appl. No.: 155,693

[22] Filed: Jun. 2, 1980

[30] Foreign Application Priority Data

Jun. 15, 1979 [GB] United Kingdom ............... 20990/79

[51] Int. Cl.$^3$ ................... C07D 303/34; C07D 303/27
[52] U.S. Cl. ........................... 260/348.43; 260/348.64; 260/348.49
[58] Field of Search ...................... 260/348.64, 348.49, 260/348.43

[56] References Cited

U.S. PATENT DOCUMENTS

| | | | |
|---|---|---|---|
| 3,033,821 | 5/1962 | Price et al. | 260/47 |
| 3,035,018 | 5/1962 | Price et al. | 260/47 |
| 3,374,204 | 3/1968 | Price et al. | 260/47 |
| 3,477,990 | 11/1969 | Dante et al. | 260/47 |
| 4,074,008 | 2/1978 | Green | 428/418 |
| 4,175,173 | 11/1979 | Bagga et al. | 528/97 |

FOREIGN PATENT DOCUMENTS 1056385  1/1967  United Kingdom ................ 260/348.15

OTHER PUBLICATIONS

Chemical Abstracts, vol. 38 (1944), 550$^5$.

Chemical Abstracts, vol. 45, (1951), 5177f.

Primary Examiner—Norma S. Milestone
Attorney, Agent, or Firm—Luther A. R. Hall

[57] ABSTRACT

New epoxide resins have the formula

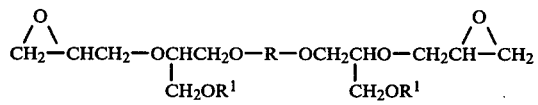

where

R represents a phenylene or naphthylene group, or two or three phenylene groups linked by carbon-carbon bonds, oxygen or sulfur atoms, sulfonyl or sulfoxide groups, or alkylene groups of 1 to 5 carbon atoms, the phenylene or naphthylene group(s) being optionally substituted by chlorine or bromine atoms or lower alkyl groups, and $R^1$ represents an alkyl group of up to 16 carbon atoms; an alkenyl group of up to 6 carbon atoms; a phenyl, naphthyl, phenylalkyl, or naphthylalkyl group, all optionally substituted by chlorine or bromine atoms, and the phenyl and naphthyl groups in addition optionally by lower alkyl groups; or a cycloalkyl or cycloalkylalkyl group.

The products, typical examples of which are 2,2-bis(p-(3-butoxy-2-glycidyloxypropyloxy)phenyl)propane and bis(p-(3-butoxy-2-glycidyloxypropyloxy)phenyl) sulfone, are generally of low viscosity and useful as casting resins.

6 Claims, No Drawings

DIGLYCIDYL ETHERS OF DI-SECONDARY ALCOHOLS, THEIR PREPARATION, AND CURABLE COMPOSITIONS CONTAINING THEM

BACKGROUND OF THE INVENTION

British Patent No. 909,567 refers to the formation of mono(hydroxyaliphatic) ethers of dihydric phenols by reaction of 1 mol. of the dihydric phenol with 1 mol. of a suitable mono-1,2-epoxide. Thus, with glycidol, a mono(2,3-dihydroxypropyl) ether is produced, while with phenyl glycidyl ether a mono(2-hydroxy-3-phenoxypropyl) ether is obtained. Reaction of the product (1 mol.), i.e., the mono(hydroxyaliphatic) ether of the dihydric phenol, with epichlorohydrin (1 mol.) in the presence of a suitable condensation catalyst (a boron trifluoride complex) is said to lead primarily to formation of the monochlorohydrin ether, leaving the phenolic hydroxyl group largely unreacted. Thus, the reaction with, for example, phenyl glycidyl ether and a dihydric phenol HO—X—OH and subsequent treatment with epichlorohydrin is indicated to proceed as follows:

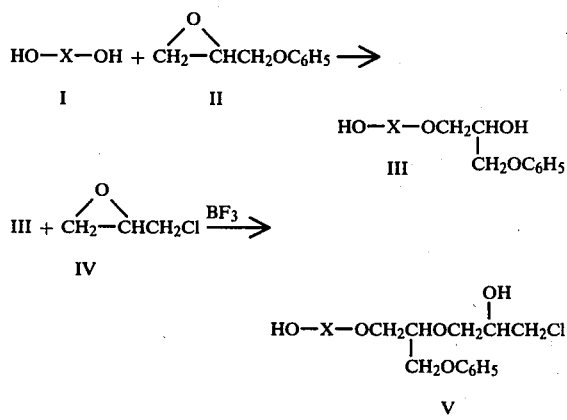

Such a mono(chlorohydrin ether) as that of formula V is then mixed with up to an equimolar amount of a bis(chlorohydrin ether) of a polyhydric phenol, and subjected to dehydrochlorination. The materials obtained, described as synthetic high molecular weight products of resinous character, are of a complex nature and generally solids of melting point 43° C. or more. Presumably, if, e.g., phenyl glycidyl ether were used, the product obtained on dehydrochlorination would contain, amongst other compounds, a glycidyl ether of a mono-secondary alcohol formed in the following manner

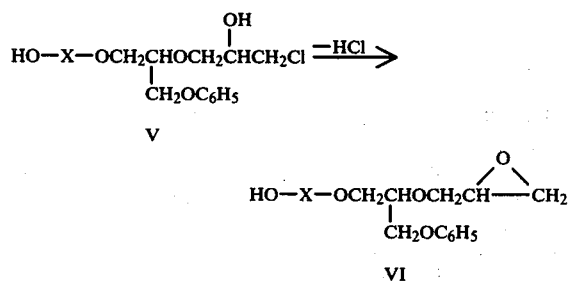

The products are said to be useful as, or in, casting compositions.

There is no suggestion that the dihydric phenol of formula I may, under the conditions employed, react with 2 molar proportions of a mono-1,2-epoxide such as that of formula II to form the corresponding bis-adduct, of formula

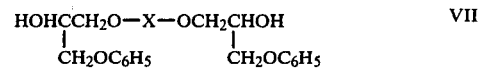

a proportion of which might, on treatment with epichlorohydrin, react to form the bis(chlorohydrin ether), which, in turn, on dehydrochlorination in the presence of the bis(chlorohydrin) ether of a polyhydric phenol, might form a corresponding diglycidyl compound.

In subsequent British Patent Specifications (Nos. 1,056,384 and 1,056,385) the same patentees reiterate that reaction of 1 mol. of a dihydric phenol with 1 mol. of a monoepoxide results in formation of a mono(hydroxyaliphatic) ether of the dihydric phenol: on treatment with an excess of epichlorohydrin in the presence of sodium hydroxide or potassium hydroxide, the epichlorohydrin is said, however, to react with the phenolic hydroxyl group exclusively, leaving the aliphatic hydroxyl group unreacted. If, for example, the reaction product, (of formula III), of phenyl glycidyl ether and a bisphenol is treated with epichlorohydrin in the presence of alkali, the reaction may be represented as follows:

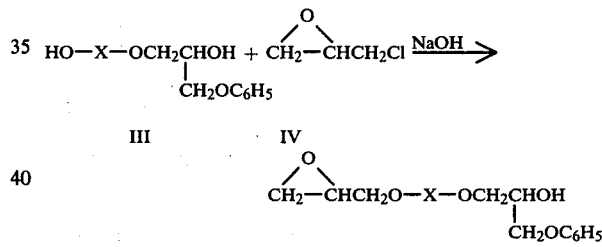

i.e., the secondary alcoholic hydroxyl group remains unchanged.

In British Patent No. 1,512,814 there are described resins containing at least two photopolymerisable groups and at least two 1,2-epoxide groups, one or more of which epoxide groups are contained in 2-(glycidyloxy)propylene units. These resins are prepared by converting hydroxy groups of 2-hydroxypropylene units into glycidyl ether groups by known methods. These resins are said to be useful as coatings, particularly in the preparation of printed circuits.

We have now found that certain new diglycidyl ethers of di(hydroxyaliphatic) ethers of dihydric phenols are curable resins, many of which are of low viscosity and are particularly suitable for use in castings. The epoxide resins most commonly employed for casting have a viscosity of 10 Pa s or more at room temperature. While compositions of lower viscosity may be made by adding a non-reactive plasticiser or solvent, or by adding various monoepoxides ("reactive diluents"), this is not always desirable, because the mechanical and thermal properties of the cured resin are often deleteriously affected.

DETAILED DISCLOSURE

Accordingly, this invention provides diglycidyl ethers of the general formula

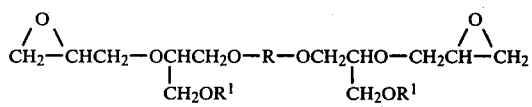
IX where R represents (i) a phenylene or naphthylene group or (ii) a radical consisting of two or three phenylene groups linked by one or two carbon-carbon bonds, ether oxygen atoms, sulphur atoms, sulphonyl groups, sulphoxide groups, carbonyl groups, or alkylene groups of 1 to 5 carbon atoms, each phenylene group or each naphthylene group optionally being substituted in the ring or rings by one or two alkyl groups, each of from 1 to 4 carbon atoms, or by one or two chlorine or bromine atoms, and each $R^1$ represents (iii) a straight chain or branched alkyl group of 1 to 16 carbon atoms, which may be substituted by one to four chlorine or bromine atoms, or (iv) a straight chain or banched alkenyl group of 2 to 6 carbon atoms, which may be substituted by one to four chlorine or bromine atoms, or (v) a phenyl or naphthyl group, optionally substituted in the ring or rings by one or two chlorine or bromine atoms or by from one or two alkyl groups, each of 1 to 4 carbon atoms, and having in all from 6 to 12 carbon atoms, or (vi) a phenylalkyl or naphthylalkyl group, optionally substituted in the ring or rings by one or two chlorine or bromine atoms or by one or two alkyl groups, each of 1 to 4 carbon atoms, said phenylalkyl or naphthylalkyl group having in all from 7 to 12 carbon atoms, or (vii) a mononuclear cycloalkyl group of 3 to 6 carbon atoms, or (viii) a mononuclear cycloalkylalkyl group of from 4 to 10 carbon atoms.

Preferably, the groups $R^1$ are the same and each represents an alkyl group of 1 to 14 carbon atoms, an allyl group, a cyclohexyl group, or a benzyl group.

Further preferred compounds of formula IX are those wherein R represents a m- or p-phenylene group or a radical consisting of two phenylene rings linked in the o—o', o—p', or p—p' position by an alkylene group of 1 to 4 carbon atoms. Compounds of formula IX where R represents a group of formula

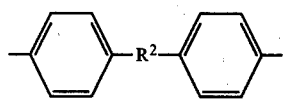
X where $R^2$ represents a methylene or isopropylidene group, and those where each $R^1$ represents an alkyl group of from 1 to 12 carbon atoms, more particularly of from 1 to 6 carbon atoms, are especially preferred.

Specific examples of diglycidyl ethers of formula IX are:

2,2-bis(p-(3-butoxy-2-glycidyloxypropyloxy)phenyl)-propane;
2,2-bis(p-(3-methoxy-2-glycidyloxypropyloxy)phenyl)-propane;
2,2-bis(p-(3-ethoxy-2-glycidyloxypropyloxy)phenyl)-propane;
2,2-bis(p-(3-dodecyloxy-2-glycidyloxypropyloxy)-phenyl)propane;
2,2-bis(p-(3-tetradecyloxy-2-glycidyloxypropyloxy)-phenyl)propane;
2,2-bis(p-(3-benzyloxy-2-glycidyloxypropyloxy)-phenyl)propane;
bis(p-(3-butoxy-2-glycidyloxypropyloxy)phenyl)methane;
1,3-bis(3-phenoxy-2-glycidyloxypropyloxy)benzene;
bis(p-(3-butoxy-2-glycidyloxypropyloxy)phenyl) sulphone;
2,2-bis(p-(3-cyclohexyloxy-2-glycidyloxypropyloxy)-phenyl)propane;
2,2-bis(4-(3-butoxy-2-glycidyloxypropyloxy)-3,5-dibromophenyl)propane;
2,2-bis(p-(3-allyloxy-2-glycidyloxypropyloxy)phenyl)-propane;
2,2-bis(p-(3-benzyloxy-2-glycidyloxypropyloxy)-phenyl)propane;
1,3-bis(2-glycidyloxy-3-phenoxypropyloxy)benzene; and
2,2-bis(p-(3-phenoxy-2-glycidyloxypropyloxy)phenyl)-propane.

The diglycidyl ethers of formula IX may be prepared from a di-secondary alcohol of formula

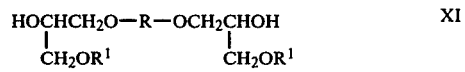
XI where R and $R^1$ are as hereinbefore defined, by treatment in known manner for replacing alcoholic hydroxy groups by glycidyloxy groups such that the two indicated hydroxy groups are replaced by glycidyloxy groups. By "known manner" is meant a method heretofore used or described in the chemical literature.

To convert a diol of formula XI into a diglycidyl ether of formula IX it is preferably caused to react with epichlorohydrin or glycerol 1,3-dichlorohydrin to form a bis(chlorohydrin) of formula

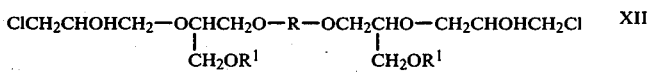
XII where R and $R^1$ have the meanings assigned above which is then dehydrochlorinated. Preferably this is carried out by either of the following methods:

(i) A two-stage process, in which a diol of formula XI is treated with at least 1.5; preferably from 1.6 to 5, and particularly from 1.8 to 2.2, molar equivalents of epichlorohydrin or glycerol 1,3-dichlorohydrin in the presence of a Lewis acid catalyst (such as boron trifluoride or a complex thereof, or stannic chloride) to afford a bis(chlorohydrin) of formula XII, the second stage being treatment with an alkali for formation of the epoxide groups. The alkali is usually sodium hydroxide, but other alkaline substances used for conversion of 1,2chlorohydrins into 1,2-epoxides may also be employed, such as barium hydroxide or potassium carbonate.

(ii) A single-stage process, in which a diol of formula XI is treated with at least 2.5, and preferably 3 to 8, molar equivalents of epichlorohydrin in the presence of an alkali (typically, sodium hydroxide) and a phase transfer catalyst, (typically a tetra-alkylammonium halide such as methyltrioctylammonium chloride, methyltridecylammonium chloride, or tetramethylammonium chloride), or a tertiary amine or quaternary ammonium base such as benzyltrimethylammonium hydroxide. At least some of the excess of the epichlorohydrin acts as hydrogen chloride-acceptor to promote formation of the glycidyl ether, being converted at the same time into glycerol 1,3-dichlorohydrin.

In both methods the reaction may be carried out in a solvent such as a hydrocarbon, an ether, or a ketone, but in the single stage process use of an excess of epichlorohydrin as the solvent is preferred. The reaction is generally performed at elevated temperatures, typically at a temperature in the range 40° to 100° C.

The diols of formula XI are, in general, known compounds (see, e.g., West German Offenlegungsschrift No. 2 838 841) and may be prepared by any of the following routes:

(i) Reaction between 1.5 to 2.5, and preferably about 1.8 to 2.2, mols of a monoglycidyl ether of formula

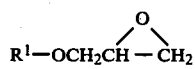   XIII and one mol of a dihydric phenol of formula

HO—R—OH   XIV where R and $R^1$ are as hereinbefore defined.

This reaction may be effected in the presence of a basic catalyst, such as a tertiary amine, a quaternary ammonium base, an alkali metal hydroxide, or quaternary ammonium salt, such as benzyltrimethylammonium chloride, usually by heating the reactants at 80° to 180° C. without a solvent.

(ii) Reaction between at least two mols of an alcohol of formula

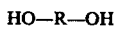   XV with one mol of a diglycidyl ether of a dihydric phenol having the formula

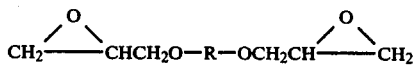   XVI where R and $R^1$ are as hereinbefore defined.

This reaction may be effected in the presence of a basic catalyst, such as a tertiary amine, a quaternary ammonium base, an alkali metal hydroxide, or a quaternary ammonium salt, usually by heating the reactants at a temperature in the range 80° to 180° C. without a solvent. Alternatively, this reaction may be carried out in the presence of a Lewis acid catalyst, such as a boron trifluoride complex or stannic chloride. When the reaction is carried out in this way, an excess of the alcohol of formula XV is usually employed and the reaction is carried out at a temperature between 50° C. and 100° C.

The excess of the alcohol is then removed by distillation prior to glycidylation.

(iii) Reaction between one mol of an alkali metal salt of a dihydric phenol of formula XIV either prepared separately or in situ, with about two mols of a chlorohydrin of formula

   XVII where $R^1$ is as hereinbefore defined.

The reactants are usually heated at a temperature of between 50° and 150° C., preferably without an added solvent.

The diglycidyl ethers of formula IX can be cured, i.e., hardened, with substances used as curing agents for epoxide resins to form insoluble, infusible products having valuable technical properties. Because of the generally low viscosity of these diglycidyl ethers they are of particular use as casting resins but they may also be used as laminating resins, surface coating resins, dipping resins, moulding compositions, potting and insulating compounds for the electrical industry, sealants and adhesives, and also in the manufacture of such products.

If desired, the diglycidyl ethers of formula IX may be cured in the presence of other epoxide resins.

There are accordingly further provided curable compositions comprising a diglycidyl ether of formula IX and a curing agent therefor and, optionally, another epoxide resin.

As examples of curing agents may be mentioned those conveniently employed as curing agents for epoxide resins, including aliphatic, cycloaliphatic, aromatic, and heterocyclic amines such as m- and p-phenylenediamine, bis(4-aminophenyl)methane, anilineformaldehyde resins, bis(4-aminophenyl) sulphone, ethylenediamine, propane-1,2-diamine, propane-1,3-diamine, N,N-diethylethylenediamine, hexamethylenediamine, diethylenetriamine, triethylenetetramine, tetraethylenepentamine, N-(2-hydroxyethyl)-, N-(2-hydroxypropyl)-, and N-(2-cyanoethyl)-diethylenetriamine, 2,2,4-trimethylhexane-1,6-diamine, 2,3,3-trimethylhexane-1,6-diamine, m-xylylenediamine, N,N-dimethyl- and N,N-diethylpropane-1,3-diamine, ethanolamine, bis(4-aminocyclohexyl)methane, 2,2-bis(4-aminocyclohexyl)propane, 2,2-bis(4-amino-3-methylcyclohexyl)propane, 3-aminomethyl-3,5,5-trimethylcyclohexylamine (isophoronediamine), and N-(2-aminoethyl)piperazine; dicyandiamide; polyaminoamides, e.g., those prepared from aliphatic polyamines and dimerised or trimerised unsaturated fatty acids; adducts of amines with stoichiometric deficits of polyepoxides such as a diglycidyl ether; isocyanates and isothiocyanates; polyhydric phenols, e.g., resorcinol, hydroquinone, 2,2-bis(4-hydroxyphenyl)propane, phenol-aldehyde resins, and oil-modified phenol-aldehyde resins, phosphoric acid; polythiols such as the "Thiokols" ("Thiokol" is a registered trade mark); and polycarboxylic acids and their anhydrides, e.g., phthalic anhydride, tetrahydrophthalic anhydride, methylendomethylenetetrahydrophthalic anhydride, nonenylsuccinic anhydride, dodecenylsuccinic anhydride, hexahydrophthalic anhydride, hexachloroendomethylenetetrahydrophthalic anhydride and endomethylenetetrahydrophthalic anhydride and their mixtures, maleic anhydride, succinic anhydride, pyromellitic acid dianhydride, benzophenone-3,3',4,4'-tetracarboxylic acid dianhydride, polysebacic anhydride, polyazelaic anhydride, the acids corresponding to the aforementioned anhydrides, and also isophthalic acid, terephthalic acid, citric acid, and mellitic acid. Particularly preferred polycarboxylic acid or anhydride curing agents are those which, in admixture if necessary, are liquid at temperatures below 60° C. There may also be used catalytic polymerising agents, such as tertiary amines (for example 2,4,6-tris(dimethylaminoethyl)-phenol and other Mannich bases, N-benzyldimethylamine, and triethanolamine); alkali metal alkoxides of alcohols (for example, the sodium alcoholate of 2,4-dihydroxy-3-hydroxymethylpentane), stannous salts of alkanoic acids (for example, stannous octanoate), Friedel-Crafts catalysts such as boron trifluoride and its complexes; and chelates formed by reaction of boron trifluoride with, e.g., 1,3-diketones.

In conjunction with the curing agents there may also be used appropriate accelerators. When poly(aminoamides), dicyandiamides, polythiols, or polycarboxylic acid anhydrides are employed for curing, tertiary amines or their salts, quaternary ammonium compounds, or alkali metal alkoxides can serve as accelerators. Examples of specific accelerators are N-benzyldimethylamine, 2,4,6-tris(dimethylaminomethyl)-phenol, imidazoles, and triamylammonium phenoxide.

Other accelerators which may be used include metal nitrates, particularly magnesium nitrate and manganese nitrate, fluorinated and chlorinated carboxylic acids and their salts, such as magnesium trifluoroacetate, sodium trifluoroacetate, magnesium trichloroacetate, and sodium trichloroacetate, trifluoromethanesulphonic acid and its salts, such as the manganese, zinc, magnesium, nickel, and cobalt salts, and magnesium perchlorate and calcium perchlorate.

An effective amount of the curing agent is employed. The proportion will depend on the chemical nature of the curing agent and the properties sought of the curable composition and its cured product; the optimum proportion can readily be determined by methods familiar to those skilled in the art. By way of illustration, however, when the curing agent is an amine there will normally be used from about 0.75 to 1.25 amino-hydrogen equivalents of the amine per 1,2-epoxy equivalent of the epoxide resin. When polycarboxylic acids or their anhydrides are used, usually from about 0.4 to 1.1 carboxylic acid, or carboxylic acid anhydride, equivalents are taken per 1,2-epoxy equivalent, while, with polyhydric phenols about 0.75 to 1.25 phenolic hydroxy equivalents of the curing agent per 1,2-epoxy equivalent are employed. Generally, from 1 to 40 parts by weight of a catalytic polymerising agent are used per 100 parts by weight of the epoxide resin.

Curing can be carried out, depending on the nature of the curing agent, at room temperature (say, 18° to 25° C.) or at higher temperatures (50° to 180° C., for example).

If desired, curing or hardening can be carried out in two stages, for example by interrupting the curing reaction or, if a curing agent requiring an elevated temperature for complete curing is used, by only partially curing at a lower temperature, to give a still fusible and soluble, curable precondensate or "B-stage" product, for use in making moulding powders, sinter-coating powders, or prepregs in a manner known per se.

As already indicated, the compounds of this invention may be used with conventional epoxide resins.

In the usual methods of manufacturing many epoxide resins, mixtures of compounds of differing molecular weight are obtained, these mixtures ordinarily containing a proportion of compounds whose epoxide groups have undergone partial hydrolysis or in which epoxidation has not proceeded to completion. The average number of 1,2-epoxide groups per molecule of an epoxide resin need not be at least 2 and need not be integral; it is generally a fractional number, but must in any case be greater than 1.0.

Of the epoxide resins which may be used in admixture with the diglycidyl ethers of formula IX the more suitable are those wherein the epoxide groups are also terminal, i.e., of formula

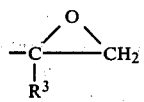
XVIII where $R^3$ denotes a hydrogen atom or a methyl group, and especially those where the groups are present as glycidyl or β-methylglycidyl groups directly attached to an atom of oxygen, nitrogen, or sulphur. Such resins include polyglycidyl and poly(β-methylglycidyl) esters obtainable by the reaction of a substance containing two or more carboxylic acid groups per molecule with epichlorohydrin, glycerol dichlorohydrin, or β-methylepichlorohydrin in the presence of alkali. The polyglycidyl esters may be derived from aliphatic carboxylic acids, e.g., oxalic acid, succinic acid, adipic acid, sebacic acid, or dimerised or trimerised linoleic acid, from cycloaliphatic carboxylic acids such as hexahydrophthalic, 4-methylhexahydrophthalic, tetrahydrophthalic, and 4-methyltetrahydrophthalic acid, or from aromatic carboxylic acids such as phthalic acid, isophthalic acid, and terephthalic acid.

Other epoxide resins which may be used include polyglycidyl and poly(β-methylglycidyl) ethers obtainable by the reaction of substances containing per molecule, two or more alcoholic hydroxy groups, or two or more phenolic hydroxy groups, with epichlorohydrin, glycerol dichlorohydrin, or β-methylepichlorohydrin, under alkaline conditions or, alternatively, in the presence of an acidic catalyst with subsequent treatment with alkali. Such polyglycidyl ethers may be derived from aliphatic alcohols, for example, ethylene glycol and poly(oxyethylene) glycols such as diethylene glycol and triethylene glycol, propylene glycol and poly(oxypropylene) glycols, propane-1,3-diol, butane-1,4-diol, pentane-1,5-diol, hexane-1,6-diol, hexane-2,4,6-triol, glycerol, 1,1,1-trimethylolpropane, and pentaerythritol; from cycloaliphatic alcohols, such as quinitol, 1,1-bis(-hydroxymethyl)cyclohex-3-ene, bis(4-hydroxycyclohexyl)methane, and 2,2-bis(4-hydroxycyclohexyl)-propane; or from alcohols containing aromatic nuclei, such as N,N-bis-(2-hydroxyethyl)aniline and 4,4'-bis(2-hydroxyethylamino)diphenylmethane. Preferably the polyglycidyl ethers are derived from substances containing two or more phenolic hydroxy groups per molecule, for example, resorcinol, catechol, hydroquinone, bis(4-hydroxyphenyl)methane, 1,1,2,2-tetrakis(4-hydroxyphenyl)ethane, 4,4'-dihydroxydiphenyl, bis(4-hydroxyphenyl) sulphone, and especially, phenol-formaldehyde or cresol-formaldehyde novolac resins, 2,2-bis(4-hydroxyphenyl)propane (otherwise known as bisphenol A), and 2,2-bis(3,5-dibromo-4-hydroxyphenyl)-propane.

There may further be employed poly(N-glycidyl) compounds, such as are, for example, obtained by the dehydrochlorination of the reaction products of epichlorohydrin and amines containing at least two hydrogen atoms directly attached to nitrogen, such as aniline, n-butylamine, bis(4-aminophenyl)methane, bis(4-aminophenyl) sulphone, and bis(4-methylaminophenyl)methane. Other poly(N-glycidyl) compounds that may be used include triglycidyl isocyanurate, N,N'-diglycidyl derivatives of cyclic alkylene ureas such as ethyleneurea and 1,3-propyleneurea, and N,N'-diglycidyl derivatives of hydantoins such as 5,5-dimethylhydantoin.

Epoxide resins obtained by the epoxidation of cyclic and acrylic polyolefins may also be employed, such as vinylcyclohexene dioxide, limonene dioxide, dicyclopentadiene dioxide, 3,4-epoxydihydrodicyclopentadienyl glycidyl ether, the bis(3,4-epoxydihydrodicyclopentadienyl) ether of ethylene glycol, 3,4-epoxycyclohexylmethyl 3',4'-epoxycyclohexanecarboxylate and its 6,6'-dimethyl derivative, the bis(3,4-epoxycyclohexanecarboxylate) of ethylene glycol, the acetal formed between 3,4-epoxycyclohexanecarboxaldehyde and 1,1-bis(hydroxymethyl)-3,4-epoxycyclohexane, bis-(2,3-epoxycyclopentyl)ether, and epoxidized butadiene or copolymers of butadiene with ethylenic compounds such as styrene and vinyl acetate.

Especially suitable epoxide resins for mixing with the diglycidyl ethers of formula IX are polyglycidyl ethers of 2,2-bis(4-hydroxyphenyl)propane or of a novolac from phenol (which may be substituted in the ring by a chlorine atom or an alkyl group of from 1 to 4 carbon atoms) and formaldehyde and having an epoxide content of at least 1.0 1,2-epoxide equivalent per kilogram.

The compositions of the invention may further contain plasticisers such as dibutyl phthalate, dioctyl phthalate, or tricresyl phosphate, inert diluents, and so-called reactive diluents, such as diglycidyl formal and especially monoepoxides such as butyl glycidyl ether, iso-octyl glycidyl ether, phenyl glycidyl ether, styrene oxide, glycidyl acrylate, glycidyl methacrylate, and glycidyl esters of synthetic, highly branched, predominantly tertiary, aliphatic monocarboxylic acids. They may also contain additives such as fillers, reinforcing materials, colouring matter, flow control agents, flame retardants, and mould lubricants. Suitable extenders, fillers, and reinforcing materials include asbestos, asphalt, bitumen, glass fibres, textile fibres, carbon fibres, boron fibres, mica, alumina, gypsum, titania, chalk, quartz flour, cellulose, kaolin, ground dolomite, wollastonite, colloidal silica having a large specific surface such as that available under the registered trade mark "Aerosil", clays modified by treatment with long chain amines (such as those available under the registered trade mark "Bentone"), powdered poly(vinyl chloride), powdered polyolefin hydrocarbons, powdered cured aminoplasts, and metal powders such as aluminium or iron powder. Flame retardants such as antimony trioxide may also be incorporated.

The following Examples illustrate the invention. Unless otherwise indicated, parts are by weight. Epoxide contents were determined by dissolving a sample in acetic acid and titrating against a standard solution of perchloric acid in acetic acid in the presence of tetraethylammonium bromide, using crystal violet as indicator.

The starting materials used in the Examples were prepared as follows:

2,2-Bis(p-(3-butoxy-2-hydroxypropyloxy)phenyl)propane

I. Bisphenol A (228 g; 1 mole), butyl glycidyl ether of epoxide content 7.4 equiv./kg (270.3 g; 2 equiv.), and benzyltrimethylammonium chloride (2.0 g) were stirred and heated together to 110° C., at which temperature an exothermic reaction commenced and the temperature rose to 120° C. When the temperature began to fall, the mixture was heated once more, its temperature being maintained at 120° C. for 1 hour and then at 150° C. for 3 hours. The mixture was cooled and was found to have a residual epoxide content of 0.11 equiv./kg, indicating that the reaction was substantially complete.

This product may also be obtained by the following procedure:

II. n-Butanol (1458 g; 19.7 moles) was stirred and heated to 60° C. Boron trifluoride-diethyl ether complex (3.6 g) was added, and to this mixture 2,2-bis(p-glycidyloxyphenyl)propane of epoxide content 5.73 equiv./kg (600 g; 3.44 equiv.) and n-butanol (60 g; 0.81 mole) were added dropwise over 5½ hours, keeping the temperature at 60° C. On complete addition, the mixture was stirred for a further 2 hours at 60° C., then heated under reduced pressure to distil off the excess of butanol. The residue weighed 839 g.

2,2-Bis(p-(3-ethoxy-2-hydroxypropyloxy)phenyl)propane

This was prepared in the same way, following Procedure II and following starting materials: ethanol (1000 g; 21.7 moles), boron trifluoride-diethyl ether complex (2.4 g), and 2,2-bis(p-glycidyloxyphenyl)propane of epoxide content 5.3 equiv./kg (400 g; 2.12 equiv.) mixed with ethanol (80 g; 1.74 moles).

The residue weighed 491 g.

2,2-Bis(p-(3-methoxy-2-hydroxypropyloxy)phenyl)propane

This was prepared in the same way, following Procedure II and using the following starting materials: methanol (500 g; 15.6 moles), boron trifluoride-diethyl ether complex (1.2 g), and 2,2-bis(p-glycidyloxyphenyl)propane of epoxide content 5.3 equiv./kg (200 g; 1.06 equiv.).

The residue weighed 232.6 g.

Bis(p-(3-butoxy-2-hydroxypropyloxy)phenyl)methane

Bis(p-hydroxyphenyl)methane (303 g; 1.5 moles), butyl glycidyl ether of epoxide content 7.45 equiv./kg (402.7 g; 6 equiv.), and benzyltrimethylammonium chloride (3 g) were stirred together and heated to 100° C., at which temperature an exothermic reaction commenced. The mixture was kept at 120° C. by moderate cooling and then, when the temperature of the mixture began to fall, heating was resumed, keeping the temperature at 120° C. for 1 hour and 150° C. for 4 hours. The mixture was cooled, and its epoxide content was found to be 0.1 equiv./kg, indicating that the reaction was virtually complete.

2,2-Bis(p-(3-dodecyloxy and tetradecyloxy-2-hydroxypropyloxy)phenyl)propane

A commercial mixture of predominantly straight chain dodecyl glycidyl ether and tetradecyl glycidyl ether of epoxide content 3.4 equiv./kg (420 g; 2.84 equiv.), bisphenol A (162.9 g; 0.71 mole), and benzyltrimethylammonium chloride (1.4 g) were blended and then heated to 150° C., when a mildly exothermic reaction commenced and the temperature of the mixture rose to 154° C. for 30 minutes. The mixture was kept at this temperature for a further 30 minutes and then raised to 160° C., at which level it was maintained for 4 hours. The residual epoxide content of the mixture was found to be 0.15 equiv./kg, indicating that the reaction was virtually complete.

Bis(p-(3-butoxy-2-hydroxypropyloxy)phenyl)sulphone 4,4'-Dihydroxydiphenyl sulphone (125.0 g; 0.5 mole), butyl glycidyl ether of epoxide content 7.45 equiv./kg (134.2 g; 1 equiv.), and benzyltrimethylammonium chloride (1.0 g) were stirred together and heated at 100° C. for 1 hour, at 120° C. for 2 hours, and then at 130° C. for 4 hours. The mixture was cooled, and was found to have an epoxide content of 0.03 equiv./kg, indicating that the reaction was substantially complete.

2,2-Bis(p-(3-cyclohexyloxy-2-hydroxypropyloxy)-phenyl)propane

Cyclohexanol (280 g; 2.8 moles) was stirred and heated to 60° C. Boron trifluoride-diethyl ether complex (0.6 g) was added, and to this mixture 2,2-bis(p-glycidyloxyphenyl)propane of epoxide content 5.73 equiv./kg (87.35 g; 0.5 equiv.) and cyclohexanol (20 g; 0.2 mole) were added dropwise over 1 hour, maintaining the temperature at 60° C. On complete addition, the mixture was stirred for a further 1 hour at 60° C., then heated under reduced pressure to remove the excess of cyclohexanol. The residue weighed 137.3 g.

2,2-Bis(4-(3-butoxy-2-hydroxypropyloxy)-3,5-dibromophenyl)propane 2,2-Bis(3,5-dibromo-4-hydroxyphenyl)propane (i.e., tetrabromobisphenol A) (136 g; 0.25 mole), butyl glycidyl ether having an epoxide content of 7.45 equiv./kg (67.1 g; 0.5 equiv.), and benzyltrimethylammonium chloride (0.5 g) were stirred at 120° C. for 1 hour and at 150° C. for 4½ hours. The mixture had a residual epoxide content of 0.01 equiv./kg, indicating that the reaction was substantially complete.

2,2-Bis(p-(3-allyloxy-2-hydroxypropyloxy)phenyl)propane

Bisphenol A (228 g; 1 mole), allyl glycidyl ether having an epoxide content of 8.64 equiv./kg (231.5 g; 2 equiv.), and benzyltrimethylammonium chloride (2 g) were stirred together and heated to 110° C., at which temperature an exothermic reaction commenced, the temperature rising spontaneously to 120° C. When the temperature began to fall, heating was resumed to keep the mixture at 120° C. After 1½ hours at this temperature the mixture was heated at 150° C. for 3 hours. The residual mixture had an epoxide content of 0.20 equiv./kg, indicating that the reaction was essentially complete.

Analogous diols may be made in a similar manner.

Thus, 2,2-bis(p-(3-benzyloxy-2-hydroxypropyloxy)phenyl)propane is prepared in the following way:

2,2-Bis(p-glycidyloxyphenyl)propane (566.1 g) of epoxide content 5.2 equiv./kg, benzyl alcohol (324 g), and tetramethylammonium chloride (1.5 g) were stirred under nitrogen at 180° C. for 7 hours. A further quantity of tetramethylammonium chloride (0.5 g) was added, and the mixture was stirred for a further 13 hours at 180° C. The product had a residual epoxide content of only 0.5 equiv./kg.

1,3-Bis(2-hydroxy-3-phenoxypropyloxy)benzene may be prepared as follows:

Resorcinol (110 g), phenyl glycidyl ether of epoxide content 6.08 equiv./kg (329.5 g), and 2-phenylimidazole (0.4 g) were stirred and heated at 130° C. for 2 hours, then at 150° C. for 3.5 hours. The product had a residual epoxide content of only 0.2 equiv./kg.

2,2-Bis(p-(2-hydroxy-3-phenoxypropyloxy)phenyl)propane may be prepared by either of the following procedures:

I. Phenyl glycidyl ether (156.6 g), bisphenol A (114 g), and benzyldimethylammonium chloride (2.7 g) were mixed together and heated carefully to 110° C., at which temperature an exothermic reaction commenced: the mixture was kept below 130° C. by cooling. When the exothermic reaction ceased, the mixture was heated at 130° C. for 2 hours, then at 150° C. for 3 hours. The resultant product had an epoxy content of only 0.145 equiv./kg, showing that the reaction had proceeded practically to completion.

II. Phenyl glycidyl ether (2243.6 g), bisphenol A (1596 g), and 2-phenylimidazole (0.5 g) were stirred together and heated carefully to 130° C., at which temperature a mildly exothermic reaction commenced that kept the mixture at 130°-132° C. for 40 minutes. It was then heated at 140° C. for 1 hour and at 180° C. for 6 hours. The resultant product had an epoxide content of only 0.15 equiv./kg.

EXAMPLE 1

2,2-Bis(p-(3-butoxy-2-hydroxypropyloxy)phenyl)propane (250 g; 1.0 equiv.), epichlorohydrin (740 g; 8 moles), and 50% aqueous tetramethylammonium chloride (6.6 g) were stirred and heated under a partial vacuum to maintain a gentle reflux at 55°-58° C. A 50% aqueous sodium hydroxide solution (84 g, 1.05 mole) was added dropwise over 3 hours, water being removed continuously as an azeotrope with epichlorohydrin. The mixture was cooled, and washed repeatedly with water to remove the sodium chloride formed. The excess of epichlorohydrin was removed by distillation under reduced pressure to leave 2,2-bis(p-(3-butoxy-2-glycidyloxypropyloxy)phenyl)propane (283 g), which had an epoxide content of 2.86 equiv./kg (theoretical value 3.28 equiv./kg). Its viscosity at 25° C. was 0.94 Pa s.

EXAMPLE 2

Example 1 was repeated, using as starting materials 2,2-bis(p-(3-butoxy-2-hydroxypropyloxy)phenyl)propane (746.5 g; 3.0 equiv.), epichlorohydrin (1110 g; 12 moles), 50% aqueous tetramethylammonium chloride (19.8 g), and 47% aqueous sodium hydroxide (268.5 g; 3.15 moles).

The yield of 2,2-bis(p-(3-butoxy-2-glycidyloxypropyloxy)phenyl)propane was 885.3 g, and it had an epoxide content of 2.95 equiv./kg and a viscosity at 25° C. of 1.74 Pa s.

EXAMPLE 3

Example 1 was repeated, using 2,2-bis(p-(3-ethoxy-2-hydroxypropyloxy)phenyl)propane (117.4 g; 0.5 equiv.), epichlorohydrin (370 g; 4 moles), 50% aqueous tetramethylammonium chloride (3.3 g), and 47% aqueous sodium hydroxide (44.8 g; 0.525 mole).

The yield of 2,2-bis(p-(3-ethoxy-2-glycidyloxypropyloxy)phenyl)propane was 142.9 g. This product had an epoxide content of 2.98 equiv./kg (theoretical value 3.44 equiv./kg) and a viscosity at 25° C. of 5.07 Pa s.

EXAMPLE 4

Example 1 was repeated, using 2,2-bis(3-methoxy-2-hydroxypropyloxy)phenyl)propane (110.4 g; 0.5 equiv.), epichlorohydrin 370 g; 4 moles), 50% aqueous tetramethylammonium chloride (3.3 g), and 47% aqueous sodium hydroxide (44.8 g; 0.525 mole).

The yield of 2,2-bis(p-(3-methoxy-2-glycidyloxypropoxy)phenyl)propane was 120 g. This product had an epoxide content of 3.28 equiv./kg (theoretical value 3.6 equiv./kg) and a viscosity at 25° C. of 6.70 Pa s.

EXAMPLE 5

Example 1 was repeated, using bis(p-(3-butoxy-2-hydroxypropyloxy)phenyl)methane (470.5 g; 2.04 equiv.), epichlorohydrin (1480 g; 16 moles), 50% aqueous tetramethylammonium chloride (13.2 g), and 47% aqueous sodium hydroxide (179 g; 2.1 moles).

The yield of bis(p-(3-butoxy-2-glycidyloxypropyloxy)phenyl)methane was 526 g. This product had an epoxide content of 2.88 equiv./kg (theoretical value 3.43 equiv./kg) and a viscosity of 25° C. of 0.85 Pa s.

Following the same procedure, 2,2-bis(p-(3-benzyloxy-2-glycidyloxypropyloxy)phenyl)propane, 1,3-bis(2-glycidyloxy-3-phenoxypropyloxy)benzene and 2,2-bis(p-(3-phenoxy-2-glycidyloxypropyloxy)phenyl)propane may be prepared from 2,2-bis(p-(3-benzyloxy-2-hydroxypropyloxy)phenyl)propane, 1,3-bis(2-hydroxy-3-phenoxypropyloxy)benzene, and 2,2-bis(p-(3-phenyloxy-2-hydroxypropyloxy)phenyl)propane, respectively.

EXAMPLE 6

Example 1 was repeated, using a mixture of 2,2-bis(p-(3-dodecyloxy-2-hydroxypropyloxy)phenyl)propane and 2,2-bis(p-(3-tetradecyloxy-2-hydroxypropyloxy)phenyl)propane (408 g; 2 equiv.), epichlorohydrin (740 g; 8 moles), 50% aqueous tetramethylammonium chloride (6.6 g), and 47% aqueous sodium hydroxide (89.5 g).

The yield of the mixture of 2,2-bis(p-(3-dodecyloxy-2-glycidyloxypropyloxy)phenyl)propane and 2,2-bis(p-(3-tetradecyloxy-2-glycidyloxypropyloxy)phenyl)propane was 386.5 g. This product had an epoxide content of 1.91 equiv./kg (theoretical value 2.15 equiv./kg) and a viscosity at 25° C. of 0.44 Pa s.

EXAMPLE 7

Example 1 was repeated, using bis(p-(3-butoxy-2-hydroxypropyloxy)phenyl)sulphone (130 g; 0.5 equiv.), epichlorohydrin (370 g; 4 moles), 50% aqueous tetramethylammonium chloride (3.3 g), and 47% aqueous sodium hydroxide (44.8 g; 0.525 mole).

The yield of bis(p-(3-butoxy-2-glycidyloxypropyloxy)phenyl)sulphone was 143 g. It had an epoxide content of 2.86 equiv./kg (theoretical value 3.21 equiv./kg) and its viscosity at 25° C. was 7.77 Pa s.

EXAMPLE 8

Example 1 was repeated, using 2,2-bis(p-(3-cyclohexyloxy-2-hydroxypropyloxy)phenyl)propane (137.3 g; 0.5 equiv.), epichlorohydrin (370 g; 4 moles), 50% aqueous tetramethylammonium chloride (3.3 g), and 47% aqueous sodium hydroxide (44.8 g; 0.525 mole).

The yield of 2,2-bis(p-(3-cyclohexyloxy-2-glycidyloxypropyloxy)phenyl)propane was 151 g. This was a low viscosity resin, having an epoxide content of 2.54 equiv./kg (theoretical value 3.07 equiv./kg).

EXAMPLE 9

Example 1 was repeated, using 2,2-bis(4-(3-butoxy-2-hydroxypropyloxy)-3,5-dibromophenyl)propane (203.1 g; 0.5 equiv.), epichlorohydrin (370 g; 4 moles), 50% aqueous tetramethylammonium chloride (3.3 g), and 47% aqueous sodium hydroxide (44.8 g; 0.525 mole).

The yield of 2,2-bis(4-(3-butoxy-2-glycidyloxypropyloxy)-3,5-dibromophenyl)propane was 221 g. This product had an epoxide content of 1.81 equiv./kg (theoretical value 2.16 equiv./kg) and its viscosity at 25° C. was 63.0 Pa s.

EXAMPLE 10

Example 1 was repeated, using 2,2-bis(p-(3-allyloxy-2-hydroxypropyloxy)phenyl)propane (461 g; 2 equiv.) epichlorohydrin (1110 g; 12 moles), 50% aqueous tetramethylammonium chloride (13.2 g), and 47% aqueous sodium hydroxide (179 g; 2.1 mole).

The yield of 2,2-bis(p-(3-allyloxy-2-glycidyloxypropyloxy)phenyl)propane was 543 g. It had an epoxide content of 3.05 equiv./kg (theoretical value 3.52 equiv./kg) and a viscosity at 25° C. of 1.3 Pa s.

EXAMPLE 11

2,2-Bis(p-(3-butoxy-2-glycidyloxypropyloxy)phenyl)propane, prepared as described in Example 1 (100 g), was heated to 60° C. and 4,4'-diaminodiphenylmethane (14.15 g), heated to 100° C., was added. The mixture was cast into a mould and heated at 80° C. for 4 hours, then at 140° C. for 16 hours. The resultant casting was clear and flexible, having a glass transition temperature of 20°-25° C. Its shear modulus, measured on a torsion pendulum, was 1140 MPa at −40° C., 950 MPa at −10° C., and 100 MPa at 20° C. The ultimate tensile strengths of four samples of this cured resin was measured at 23° C. and found to be 11.6±0.6 MPa, the elongation at break being 122±4%.

EXAMPLE 12

A further sample of the product of Example 1 (100 g) was mixed at room temperature with triethylenetetramine (5.93 g) and cast into a mould. It was allowed to stand at room temperature overnight, then heated at 80° C. for 2 hours and 100° C. for 1 hour. The resultant casting was clear and flexible, having a glass transition temperature of −7° to −5° C. Its shear modulus, measured on a torsion pendulum, was 1130 MPa at −40° C., 250 MPa at −10° C., and 0.7 MPa at 20° C. The ultimate tensile strengths of three samples of this cured resin measured at 22° C. were found to be 0.46±0.01 MPa, the elongation at break being 36.3±0.2%.

EXAMPLE 13

A further sample of the product of Example 1 (50 g) was heated to 80° C. and hexahydrophthalic anhydride (21.5 g), also heated to 80° C., was added. N-benzyldimethylamine (1 g), an accelerator, was added to the mixture, which was then stirred and cast in a mould. After being heated at 80° C. for 3 hours and at 120° for 4 hours a clear, flexible casting was obtained, having a glass transition temperature of 30° to 32° C. The shear modulus of this casting, measured on a torsion pendulum, was 1060 MPa at −40° C., 1000 MPa at −10° C., and 750 MPa at 20° C. The ultimate tensile strengths of five samples were measured at 21° C. and found to be 23.9±1.6 MPa, the elongation at break being approximately 135%.

EXAMPLE 14

The products of Examples 3, 4, and 5 (25 g) were separately heated to 60° C. and mixed with an equivalent quantity of 4,4'-diaminodiphenylmethane (DDM). The mixtures were then cast in moulds and cured by heating at 80° C. for 4 hours and at 140° C. for 16 hours.

The results are shown in the following Table:

TABLE 1

| Product of Example | Quantity of DDM (g) | Appearance of cured casting | Glass transition temperature (°C.) |
|---|---|---|---|
| 3 | 3.8 | clear, flexible | 55 |
| 4 | 4.17 | clear, flexible | 65 |
| 5 | 3.67 | clear, flexible | 26 |

EXAMPLE 15

The product of Example 4 (25 g) was heated to 80° C. and boron trifluoride-ethylamine complex (1 g) was added. The mixture was stirred until all of the complex had dissolved in the resin, and then it was cast into a mould. After heating at 120° C. for 3 hours and 150° C. for 3 hours, a clear flexible casting with a glass transition temperature of 28° C. was obtained.

What is claimed is:

1. A compound of the general formula

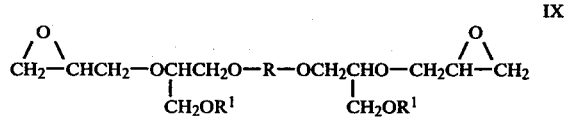
IX where

R represents (i) a phenylene or naphthylene group, or (ii) a phenylene or naphthylene group substituted in the nucleus by one or two alkyl groups, each of from 1 to 4 carbon atoms, or (iii) a phenylene or naphthylene group substituted in the nucleus by one or two chlorine atoms or by one or two bromine atoms, or (iv) a radical consisting of two or three phenylene groups linked by one or two carbon-carbon bonds, ether oxygen atoms, sulfur atoms, sulfonyl groups, sulfoxide groups, or alkylene groups of 1 to 5 carbon atoms, or (v) a radical consisting of two or three phenylene groups linked by one or two carbon-carbon bonds, ether oxygen atoms, sulfur atoms, sulfonyl groups, sulfoxide groups, or alkylene groups of 1 to 5 carbon atoms, substituted in one or two phenylene groups by a total of at most two alkyl groups, each of from 1 to 4 carbon atoms, or (vi) a radical consisting of two or three phenylene groups linked by one or two carbon-carbon bonds, ether oxygen atoms, sulfur atoms, sulfonyl groups, sulfoxide groups, or alkylene groups of 1 to 5 carbon atoms, substituted in one or two phenylene groups by a total of at most two halogen atoms selected from chlorine and bromine, each $R^1$ represents (vii) a straight chain or branched alkyl group of 1 to 16 carbon atoms, (viii) a straight chain or branched alkyl group of 1 to 16 carbon atoms, substituted by a total of at most four halogen atoms selected from chlorine and bromine, or (ix) a straight chain or branched alkenyl group of 2 to 6 carbon atoms, (x) a straight chain or branched alkenyl group of 2 to 6 carbon atoms, substituted by a total of at most four halogen atoms selected from chlorine and bromine, or (xi) a phenyl or naphthyl group, or (xii) a phenyl or naphthyl group, substituted in the nucleus by one or two chlorine atoms or by one or two bromine atoms, or (xiii) a phenyl or naphthyl group, substituted in the nucleus by one or two alkyl groups, each of 1 to 4 carbon atoms, and having in all at most 12 carbon atoms, or (xiv) a phenylalkyl or naphthylalkyl group having in all at most 12 carbon atoms, or (xv) a phenylalkyl or naphthylalkyl group, substituted in the nucleus by one or two chlorine or by one or two bromine atoms, having in all from 7 to 12 carbon atoms, or (xvi) a phenylalkyl or naphthylalkyl group, substituted in the nucleus by one or two alkyl groups each of 1 to 4 carbon atoms, said phenylalkyl or naphthylalkyl group having in all at most 12 carbon atoms, or (xvii) a mononuclear cycloalkyl group of 3 to 6 carbon atoms, or (xviii) a mononuclear cycloalkylalkyl group of from 4 to 10 carbon atoms.

2. A compound according to claim 1, wherein the groups $R^1$ in formula IX are the same and each represents an alkyl group of 1 to 14 carbon atoms, or an allyl, cyclohexyl, or benzyl group.

3. A compound according to claim 1, wherein R in formula IX represents a m- or p- phenylene group.

4. A compound according to claim 1, wherein R in formula IX represents a radical consisting of two phenylene rings linked in the o—o', o—p', or p,p'-position by an alkylene group of 1 to 4 carbon atoms.

5. A compound according to claim 1, wherein R in formula IX represents a group of formula

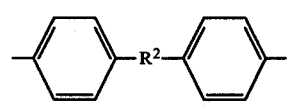
X where $R^2$ represents a methylene or an isopropylidene group.

6. A compound according to claim 1, which is:

2,2-bis(p-(3-butoxy-2-glycidyloxypropyloxy)phenyl)propane;

2,2-bis(p-(3-methoxy-2-glycidyloxypropyloxy)phenyl)propane;

2,2-bis(p-(3-ethoxy-2-glycidyloxypropyloxy)phenyl)propane;

2,2-bis(p-(3-dodecyloxy-2-glycidyloxypropyloxy)phenyl)propane;

2,2-bis(p-(3-tetradecyloxy-2-glycidyloxypropyloxy)phenyl)propane;

2,2-bis(p-(3-benzyloxy-2-glycidyloxypropyloxy)phenyl)propane;

bis(p-(3-butoxy-2-glycidyloxypropyloxy)phenyl)methane;

1,3-bis(3-phenoxy-2-glycidyloxypropyloxy)benzene;

bis(p-(3-butoxy-2-glycidyloxypropyloxy)phenyl)sulfone;

2,2-bis(p-(3-cyclohexyloxy-2-glycidyloxypropyloxy)phenyl)propane;

2,2-bis(4-(3-butoxy-2-glycidyloxypropyloxy)-3,5-dibromophenyl)propane;

2,2-bis(p-(3-allyloxy-2-glycidyloxypropyloxy)phenyl)propane;

2,2-bis(p-(3-benzyloxy-2-glycidyloxypropyloxy)phenyl)propane;

1,3-bis(2-glycidyloxy-3-phenoxypropyloxy)benzene; or 2,2-bis(p-(3-phenoxy-2-glycidyloxypropyloxy)phenyl)propane.

* * * * *